(12) United States Patent
Jansens et al.

(10) Patent No.: US 7,049,491 B2
(45) Date of Patent: May 23, 2006

(54) PLANTS MADE INSECT RESISTANT BY TRANSFORMATION WITH A NUCLEIC ACID ENCODING A MODIFIED CRY1AB PROTEIN AND METHODS FOR MAKING SAME

(75) Inventors: Stefan Jansens, Ghent (BE); Sara Van Houdt, Zottegem (BE); Arlette Reynaerts, Drongen (BE)

(73) Assignee: Bayer Bioscience N.V., Ghent (BE)

( * ) Notice: Subject to any disclaimer, the term of this patent is extended or adjusted under 35 U.S.C. 154(b) by 64 days.

(21) Appl. No.: 10/429,096

(22) Filed: May 5, 2003

(65) Prior Publication Data

US 2003/0226171 A1   Dec. 4, 2003

Related U.S. Application Data

(60) Provisional application No. 60/509,067, filed on May 3, 2002.

(51) Int. Cl.
*A01H 5/00* (2006.01)
*A01H 5/10* (2006.01)
*C12N 15/82* (2006.01)
*C12N 15/32* (2006.01)

(52) U.S. Cl. .................... 800/302; 800/279; 536/23.71
(58) Field of Classification Search ................ 800/279, 800/320.1, 320.2, 314; 435/320.1, 412, 419; 536/23.6
See application file for complete search history.

(56) References Cited

U.S. PATENT DOCUMENTS

| | | | |
|---|---|---|---|
| 5,500,365 | A | 3/1996 | Fischhoff et al. |
| 5,595,733 | A | 1/1997 | Carswell et al. |
| 6,114,608 | A | 9/2000 | Mettler et al. |
| 6,180,774 | B1 | 1/2001 | Brown et al. |
| 6,320,100 | B1 | 11/2001 | Koziel et al. |

FOREIGN PATENT DOCUMENTS

EP   0451878 A1   10/1991

OTHER PUBLICATIONS

Michael G. Koziel et al., "Field Performance of Elite Transgenic Maize Plants Expressing an Insecticidal Protein Derived from *Bacillus thuringiensis*", Bio/Technology, vol. 11, pp. 194-200, Feb. 1993, Nature Publishing Co., NY, USA.

Herman Hofte et al, Structural and Functional Analysis of a Cloned Delta Endotoxin of *Bacillus thuringiensis* Berliner 1715, FEBS, vol. 161, No. 2,, pp. 273-280, Dec. 1, 1986 European Journal of Biochemistry, Berlin, DE.

Herman Hofte et al., Insecticidal Crystal Proteins of *Bacillus thuringiensis*, Microbiological Reviews , vol. 53, Jun. 1, 1989, pp. 242-255, American Society for Microbiology, Washington, DC, USA.

Stefan Jansens et al., "Transgenic Corn Expressing a Cry9C Insecticidal Protein from *Bacillus thuringiensis* Protected from European Corn Borer Damage", Crop Science, vol. 37, No. 5, p. 1616-1623 (1997) Crop Science Society of America, Madison, Wisconsin, USA.

Mark Vaeck et al., "Transgenic Plants Protected from Insect Attack", Nature, vol. 327, No. 6125, pp. 33-37, Jul. 2, 1987, Macmillan Journals Ltd., 1987.

E. Schnepf et al., "*Bacillus thuringiensis* and its Pesticidal Crystal Proteins", Microbiology and Molecular Biology Reviews, Sep. 1998, pp. 775-806, vol. 62, No. 3, American Society for Microbiology.

Neil Crickmore et al., "Revision of the Nomenclature for the *Bacillus thuringiensis cry* genes", Society for Invertebrate Pathology, SIP 28th Annual Meeting, Jul. 16-21, 1995, Cornell University, Ithaca, NY, USA.

Theo van der Salm et al, "Insect Resistance of Transgenic Plants that Express Modified *Bacillus thuringiensis cryIA(b)* and *cryIC* genes: a Resistance Managment Strategy", Plant Molecular Biology, vol. 26, pp. 51-59 (1994) Kluwer Academic Publishers, Dordrecht, Holland.

Arvidson et al, "Specificity of *Bacillus thuringiensis* for Lepidopteran Larvae: Factors Involved *in vivo* and in the Structure of a Purified Protoxin" (1989) Mol Microbiol 3:1533-1542.

(Continued)

Primary Examiner—Anne Kubelik
(74) Attorney, Agent, or Firm—Buchanan Ingersoll P.C.

(57) ABSTRACT

The present invention relates to a DNA sequence encoding a modified Cry1Ab protein that has insecticidal activity. The invention further relates to a method for producing insect resistant plants by introducing into the genome of the plants a foreign DNA comprising such a modified cry1Ab coding sequence. The invention further relates to plants or parts thereof comprising in their genome the modified cry1Ab coding sequence of the present invention.

10 Claims, No Drawings

OTHER PUBLICATIONS

Bogorad, "Engineering Chloroplasts: an Alternative Site for Foreign Genes, Proteins, Reactions and Products" (2000) *Trends Biotechn* 18(6):257-263, Elsevier Science Ltd., Oxford, United Kingdom.

Casas et al., "Cereal Transformation Through Particle Bombardment" (1995) *Plant Breeding Reviews* 13:235-264, John Wiley & Sons, Inc.

A. Christensen et al, "Maize Polyubiquitin Genes: Structure, Thermal Perturbation of Expression and Transcript Splicing, and Promoter Activity Following Transfer to Protoplasts by Electroporation" (1992) *Plant Molecular Biology* 18:675-689, Kluwer Academic Publishers, Printed in Belgium.

P. Christou, "Rice Transformation: Bombardment" (1997) *Plant Molecular Biology* 35:197-203, Kluwer Academic Publishers, Printed in Belgium.

Maria Jose Cordero et al., "Expression of a Maize Proteinase Inhibitor Gene is Induced in Response to Wounding and Fungal Infection: Systemic Wound-Response of a Monocot Gene" (1994) *The Plant Journal* 6(2):141-150, Blackwell Sciences, Ltd., Oxford, United Kingdom.

Cornelissen & Vandewiele, "Nuclear Transcriptional Activity of the Tobacco Plastid *psbA* Promoter" (1989) *Nucleic Acids Research*, 17:19-23, IRL Press Limited, Oxford, England.

Crickmore, "Revision of the Nomenclature for the *Bacillus thuringiensis cry* Genes" (1995) 28th Annual Meeting of the Society for Invertebrate Pathology, Society for Invertebrate Pathology, Bethesda Maryland, USA, p. 14.

D'Halluin et al, "Transgenic Maize Plants by Tissue Electroporation" (1992) *Plant Cell*, 4:1495-1505, American Society of Plant Physiologists, Rockville, Maryland, USA.

Datta et al., "Transformation of Rice via PEG-Mediated DNA Uptake into Protoplasts" (1999) *Methods Mol Biol* 111:335-347, Humana Press Inc., Totowa NJ.

De Block et al, "Transformation of Brassica-Napus and Brassica-Oleracea Using Agrobacterium-Tumefaciens and the Expression of the Bar and Neo Genes in the Transgenic Plants" (1989) *Plant Physiol* 91 (2):694-701.

De Greve et al, "Nucleotide Sequence and Transcript Map of the *Agrobacterium tumefaciens* Ti Plasmid-Encoded Octopine Synthase Gene" (1983), *J Mol Applied Gen* 499-511, Raven Press, New York, USA.

de Pater et al, "The Promoter of the Rice Gene *GOS2* is Active in Various Different Monocot Tissues and Binds Rice Nuclear Factor ASF-1" (1992) *Plant J* 2:837-844, Blackwell Sciences, Ltd., Oxford United Kingdom.

Dunwell, Transformation of Maize Using Silicon Carbide Whiskers (1999) *Methods Mol Biol* 111:375-82, Humana Press Inc., Totowa NJ.

Finer et al, "Particle Bombardment Mediated Transformation" (1999) *Cur Top Microbiol Immunol* 240:59-80.

Grochulski et al, (1995) "Bacillus thuringiensis CryIA(a) Insecticidal Toxin: Crystal Structure and Channel Formation", *J. Mol. Biol.* 254:447, Academic Press Limited.

Guevara-Garcia et al., "Tissue-Specific and Wound-Inducible Pattern of Expression of the Mannopine Synthase Promoter is Determined by the Interaction Between Positive and Negative *cis*-Regulatory Elements" (1993) *Plant J* 4(3):495-505, Blackwell Sciences, Ltd, Oxford, United Kingdom.

Guthrie "Breeding for Insect Resistance in Maize" (1989) *Plant Breed Rev* 6:209-243, Timber Press, Portland, Oregon, USA.

Harpster et al, "Relative Strengths of the 35S Califlower Mosaic Virus, 1', 2', and Nopaline Synthase Promoters in Transformed Tobacco Sugarbeet and Oilseed Rape Callus Tissue" (1988) *Mol Gen Genetics* 212:182-190, Springer Verlag, Berlin Germany.

Hiei et al, Transformation of Rice Mediated by *Agrobacterium tumefaciens* (1997) *Plant Mol Biol* 35:205-218, Kluwer Academic Publishers, Printed in Belgium.

Hofte & Whiteley, Insecticidal Crystal Proteins of *Bacillus thuringiensis* (1989) *Microbiol Rev* 53(2):242-55, American Society for Microbiology.

Hofte et al., "Structural and Functional Analysis of a Cloned Delta Endotoxin of *Bacillus Thuringiensis berliner* 1715" (1986) *Eur J. Biochem* 161:273-280, FEBS, West Germany.

Hood et al, The Hypervirulence of *Agrobacterium tumefaciens* A281 is Encoded in a Region of pTiBo542 Outside of T-DNA (1986) *J. Bacterial.* 168(3):1291-1301, American Society of Microbiology, Washington, DC, USA.

Jansens et al, "Transgenic Corn Expressing a Cry9C Insecticidal Protein from *Bacillus thuringiensis* Protected from European Corn Borer Damage"(1997) *Crop Science* 37(5):1616-1624, Crop Science Society of America, Madison, Wisconsin, USA.

Johnson et al, Expression of Proteinase Inhibitors I and II in Transgenic Tobacco Plants: Effects on Natural Defense Against *Manduca sexta* Larvae (1989) *PNAS* 86:9871-9875, National Academy of Sciences, Washington DC, USA.

Komari et al., "Advances in Cereal Gene Transfer", (1998) *Curr Opin Plant Biol* 1(2):161-165, Current Biology Ltd. ISSN 1369-5266.

Langridge et al, "Dual Promoter of *Agrobacterium tumefaciens* Mannopine Synthase Genes is Regulated by Plant Growth Hormones" (1989), *Proc Natl Acad Sci USA* 86:3219-3223, National Academy of Sciences, Washington, DC, USA.

Newell "Plant Transformation Technology" (2000) *Mol Biotechnol* 16(1):53-65, Humana Press Inc., Totowa, NJ, USA.

Odell et al, "Identification of DNA Sequences Required for Activity of the Cauliflower Mosaic Virus 35S Promoter"(1985) *Nature* 313:810-812, Nature Publishing Group, Hampshire, United Kingdom.

Potrykus, "Gene Transfer Methods for Plants and Cell Cultures" (1990) *Cyba Found Symp* 154:198-208, ISSN 0300-5208, Journal Code: 0356636.

Poulsen "Genetic Transformation of *Brassica*" (1996) *Plant Breeding* 115-209-225, Blackwell, Wissenschafts-Verlag, Berlin.

Sawahel et al, "Gene Cloning in Plants: Innovative Approaches" (1995) *Biotechniques* 19(1):106-110.

Schnepf et al. "*Bacillus thuringiensis* and Its Pesticidal Crystal Proteins" (1998) *Microbiol Mol Biol Rev* 62(3):775-806, American Society for Microbiology, Washington, DC, USA.

Thompson et al, "Characterization of the Herbicide-Resistance gene *bar* from *Streptomyces hygroscopicus*" (1987) *EMBO J* 6:2519-2523, Oxford University Press, Oxford, United Kingdom.

van der Salm et al, "Insect Resistance of Transgenic Plants That Express Modified *Bacillus thuringiensis cryIA(b)* and *cryIC* Genes: A Resistance Management Strategy" (1994) *Plant Mol Biol* 26:51-59, Kluwer Academic Publishers, Printed in Belgium.

Vasil et al, "Transformation of Wheat via Particle Bombardment" (1999) *Methods Mol Biol* 111:349-358, Humana Press Inc., Totowa, NJ.

Velten et al, "Isolation of a Dual Plant Promoted Fragment from the Ti Plasmid of *Agrobacterium tumefaciens*" (1984) *EMBO J* 12:2723-2730 Oxford University Press, Oxford, United Kingdom.

Barton et al, "*Bacillus thuringiensis* δ-Endotoxin Expressed in Transgenic *Nicotiana tabacum* Provides Resistance to Lepidopteran Insects", 1987 Plant Physiol. 85: 1103-1109, American Society of Plant Physiologists, Rockville, MD, USA.

Bates, "Electroporation of Plant Protoplasts and Tissues", 1995, Methods Cell Biol. 1995;50:363-73, Academic Press, London and New York.

Bradford, 1976, "A Rapid and Sensitive Method for the Quantitation of Microgram Quantities of Protein Utilizing the Principle of Protein-Dye Binding" Anal. Biochem. 72:248-254, Academic Press, London and New York.

Breitler et al. "The −689/+197 Region of the Maize Protease Inhibitor Gene Directs High Level, Wound-Inducible Expression of the *cry1B* Gene Which Protects Transgenic Rice Plants From Stemborer Attack", 2001, Mol Breeding 7:259-274, Kluwer Academic Publishers, Netherlands.

Clark et al., "ELISA Techniques", 1986, Methods Enzymol. 118:742-766, Academic Press, London and New York.

De Maagd et al., "*Bacillus thuringiensis* Toxin-Mediated Insect Resistance in Plants", 1999, Trends Plant Sci 4:9-13, Elsevier Science, Kidlington and Oxford, England.

Depicker et al. "Nopaline Synthase: Transcript Mapping and DNA Sequence" 1982, J Mol Appl Gen 1:561-573, Raven Press, New York.

Duan et al., "Transgenic Rice Plants Harboring an Introduced Potato Proteinase Inhibitor II Gene are Insect Resistant", 1996, Nature Biotech 14:494-498, Nature America, New York.

Franck et al. "Nucleotide Sequence of Cauliflower Mosaic Virus DNA",1980, Cell 21:285-294, Cell Press, Cambridge, MA.

Wilbur and Lipmann, "Rapid Similarity Searches of Nucleic Acid and Protein Data Banks", 1983, Proc Nat'l Acad Sci USA 80:726, National Academy of Sciences, Washington DC.

Witowsky & Siegfried, "Managing Corn Borer Resistance", 1997, PBI Bulletin 14-15.

SEQUENCE LISTING

<160> NUMBER OF SEQ ID NOS: 2

<210> SEQ ID NO 1
<211> LENGTH: 617
<212> TYPE: PRT
<213> ORGANISM: Artificial sequence
<220> FEATURE:
<223> OTHER INFORMATION: modified protein from Bacillus thuringiensis

<400> SEQUENCE: 1

```
Met Ala Asp Asn Asn Pro Asn Ile Asn Glu Cys Ile Pro Tyr Asn Cys
1               5                   10                  15

Leu Ser Asn Pro Glu Val Glu Val Leu Gly Gly Glu Arg Ile Glu Thr
            20                  25                  30

Gly Tyr Thr Pro Ile Asp Ile Ser Leu Ser Leu Thr Gln Phe Leu Leu
        35                  40                  45

Ser Glu Phe Val Pro Gly Ala Gly Phe Val Leu Gly Leu Val Asp Ile
50                  55                  60

Ile Trp Gly Ile Phe Gly Pro Ser Gln Trp Asp Ala Phe Leu Val Gln
65                  70                  75                  80

Ile Glu Gln Leu Ile Asn Gln Arg Ile Glu Glu Phe Ala Arg Asn Gln
            85                  90                  95

Ala Ile Ser Arg Leu Glu Gly Leu Ser Asn Leu Tyr Gln Ile Tyr Ala
            100                 105                 110

Glu Ser Phe Arg Glu Trp Glu Ala Asp Pro Thr Asn Pro Ala Leu Arg
        115                 120                 125

Glu Glu Met Arg Ile Gln Phe Asn Asp Met Asn Ser Ala Leu Thr Thr
130                 135                 140

Ala Ile Pro Leu Phe Ala Val Gln Asn Tyr Gln Val Pro Leu Leu Ser
145                 150                 155                 160

Val Tyr Val Gln Ala Ala Asn Leu His Leu Ser Val Leu Arg Asp Val
            165                 170                 175

Ser Val Phe Gly Gln Arg Trp Gly Phe Asp Ala Ala Thr Ile Asn Ser
        180                 185                 190

Arg Tyr Asn Asp Leu Thr Arg Leu Ile Gly Asn Tyr Thr Asp His Ala
        195                 200                 205

Val Arg Trp Tyr Asn Thr Gly Leu Glu Arg Val Trp Gly Pro Asp Ser
210                 215                 220

Arg Asp Trp Ile Arg Tyr Asn Gln Phe Arg Arg Glu Leu Thr Leu Thr
225                 230                 235                 240

Val Leu Asp Ile Val Ser Leu Phe Pro Asn Tyr Asp Ser Arg Thr Tyr
            245                 250                 255

Pro Ile Arg Thr Val Ser Gln Leu Thr Arg Glu Ile Tyr Thr Asn Pro
        260                 265                 270

Val Leu Glu Asn Phe Asp Gly Ser Phe Arg Gly Ser Ala Gln Gly Ile
        275                 280                 285

Glu Gly Ser Ile Arg Ser Pro His Leu Met Asp Ile Leu Asn Ser Ile
290                 295                 300

Thr Ile Tyr Thr Asp Ala His Arg Gly Glu Tyr Tyr Trp Ser Gly His
305                 310                 315                 320

Gln Ile Met Ala Ser Pro Val Gly Phe Ser Gly Pro Glu Phe Thr Phe
            325                 330                 335

Pro Leu Tyr Gly Thr Met Gly Asn Ala Ala Pro Gln Gln Arg Ile Val
            340                 345                 350
```

```
Ala Gln Leu Gly Gln Gly Val Tyr Arg Thr Leu Ser Ser Thr Leu Tyr
        355                 360                 365

Arg Arg Pro Phe Asn Ile Gly Ile Asn Asn Gln Gln Leu Ser Val Leu
    370                 375                 380

Asp Gly Thr Glu Phe Ala Tyr Gly Thr Ser Ser Asn Leu Pro Ser Ala
385                 390                 395                 400

Val Tyr Arg Lys Ser Gly Thr Val Asp Ser Leu Asp Glu Ile Pro Pro
                405                 410                 415

Gln Asn Asn Asn Val Pro Pro Arg Gln Gly Phe Ser His Arg Leu Ser
            420                 425                 430

His Val Ser Met Phe Arg Ser Gly Phe Ser Asn Ser Ser Val Ser Ile
        435                 440                 445

Ile Arg Ala Pro Met Phe Ser Trp Ile His Arg Ser Ala Glu Phe Asn
    450                 455                 460

Asn Ile Ile Pro Ser Ser Gln Ile Thr Gln Ile Pro Leu Thr Lys Ser
465                 470                 475                 480

Thr Asn Leu Gly Ser Gly Thr Ser Val Val Lys Gly Pro Gly Phe Thr
                485                 490                 495

Gly Gly Asp Ile Leu Arg Arg Thr Ser Pro Gly Gln Ile Ser Thr Leu
            500                 505                 510

Arg Val Asn Ile Thr Ala Pro Leu Ser Gln Arg Tyr Arg Val Arg Ile
        515                 520                 525

Arg Tyr Ala Ser Thr Thr Asn Leu Gln Phe His Thr Ser Ile Asp Gly
    530                 535                 540

Arg Pro Ile Asn Gln Gly Asn Phe Ser Ala Thr Met Ser Ser Gly Ser
545                 550                 555                 560

Asn Leu Gln Ser Gly Ser Phe Arg Thr Val Gly Phe Thr Thr Pro Phe
                565                 570                 575

Asn Phe Ser Asn Gly Ser Ser Val Phe Thr Leu Ser Ala His Val Phe
            580                 585                 590

Asn Ser Gly Asn Glu Val Tyr Ile Asp Arg Ile Glu Phe Val Pro Ala
        595                 600                 605

Glu Val Thr Phe Glu Ala Glu Tyr Asp
    610                 615

<210> SEQ ID NO 2
<211> LENGTH: 1854
<212> TYPE: DNA
<213> ORGANISM: Artificial sequence
<220> FEATURE:
<223> OTHER INFORMATION: sequence encoding modified protein from
      Bacillus thuringiensis

<400> SEQUENCE: 2
atggctgaca caaccccaa catcaacgag tgcatcccct acaactgcct gagcaaccca      60
gaggtggagg tgctgggtgg tgagaggatc gagaccggtt acacccccat cgacatcagc     120
ctgagcctga cccagttcct gctgagcgag ttcgtgcctg gtgctggctt cgtgctggga     180
ctagtggaca tcatctgggg catcttcggt cccagccagt gggatgcctt cctggtgcag     240
atcgaacagt taattaacca agaatagaa gaattcgcta ggaaccaagc catctctaga     300
ctggagggcc tgagcaacct gtaccagatc tacgccgaga gcttccgcga gtgggaggct     360
gaccccacca acccagccct cgcgaggag atgcgcatcc agttcaacga catgaactct     420
gccctgacca ccgccatccc actcttcgct gtccagaact accaggtccc tctcctgtct     480
```

```
gtctatgtgc aagctgccaa cctccatctc agcgtccttc gcgacgtgag cgtctttggg    540
cagaggtggg ggttcgacgc tgccaccatc aacagccgct acaacgacct gacgcgtctg    600
atcggcaact acaccgacca cgcagtgaga tggtacaaca ctgggcttga gagggtctgg    660
ggtcccgaca gccgcgactg gatcaggtac aaccagttca ggcgtgaact cactctcacc    720
gtcttggata tcgtcagtct cttccccaac tacgacagca ggacctaccc tatccggact    780
gtgagccagc tgacccgcga gatctacacc aaccccgtgc tggagaactt cgacggcagc    840
ttcaggggct ctgcccaggg catcgagggc agcatccgca gcccccacct gatggacatc    900
ctgaacagca tcaccatcta cactgacgcc cacagggtg agtactactg gtctggccac    960
cagatcatgg cttctcccgt gggcttcagc ggtcccgagt tcaccttccc cctgtacggc   1020
acaatgggca acgctgcccc acagcagagg atcgtggccc agctgggcca gggcgtgtac   1080
cgcaccctga gcagcaccct gtacaggagg cccttcaaca tcggcatcaa caaccagcag   1140
ctgagcgtgc tggatggcac cgagttcgcc tacggcacca gcagcaacct gcccagcgcc   1200
gtataccgca agagcggcac tgtggacagc ctggacgaga tcccacccca gaacaacaac   1260 gtgccccta ggcaggggtt ctctcatcgc ctctcacacg tgagcatgtt ccgcagcggc   1320
ttcagcaaca gcagcgtgag catcatcagg gctcccatgt tcagctggat ccaccgcagc   1380
gctgagttca acaacatcat tccaagtagc cagatcactc agatcccact caccaagagc   1440
accaacctgg gctccgggac tagcgttgtc aagggaccag ggttcactgg aggcgacatc   1500
ctgaggagga ccagcccagg ccagatcagc accttaaggg tgaacatcac cgctcccctc   1560
agccaacgct acaggqtcag gatcaggtac gcttccacca ccaacctgca gttccacacc   1620
agcatcgacg gcaggcccat caaccagggc aacttcagcg ccaccatgag cagcggcagc   1680
aacctgcaga gcggaagctt ccgcactgtg ggcttcacta ccccattcaa cttctccaac   1740
ggcagcagcg tgttcaccct gtctgcccac gtgttcaaca gcggcaacga ggtgtacatc   1800
gacaggatcg agtttgtccc agctgaggtg accttcgaag ctgagtacga ctga          1854
```

PLANTS MADE INSECT RESISTANT BY TRANSFORMATION WITH A NUCLEIC ACID ENCODING A MODIFIED CRY1AB PROTEIN AND METHODS FOR MAKING SAME

CONTINUING APPLICATION DATA

This application claims benefit of provisional Application No. 60/509,067, filed 3 May 2002, the contents of which are incorporated herein by reference.

FIELD OF THE INVENTION

The present invention relates to a DNA sequence encoding a modified Cry1Ab protein that has insecticidal activity. The invention further relates to a method for producing insect resistant plants by introducing into the genome of the plants a foreign DNA comprising such a modified cry1Ab coding sequence. The invention further relates to plants or parts thereof comprising in their genome the modified cry1Ab coding sequence of the present invention.

BACKGROUND ART

The Gram-positive soil bacterium *Bacillus thuringiensis* is well known for its production of proteins or delta-endotoxins, that are toxic to a variety of lepidopteran, coleopteran, and dipteran larvae. Different strains of *B. thuringiensis* have been shown to produce different insecticidal crystal proteins, which are specifically toxic to certain species of insects (reviewed by Höfte and Whiteley, 1989; Schnepf et al., 1998).

The specific toxicity of insecticidal toxins produced by *B. thuringiensis* for target insects and their non-toxicity to plants and other organisms has made compositions comprising different Bt strains the product of choice for the biological control of agricultural insect pests. Various of the genes encoding the crystal proteins have been cloned and their DNA sequences determined (Höfte and Whiteley, 1989; Crickmore et al., 1995). This has led to the engineering of modified delta-endotoxin encoding genes and the development of plants expressing these delta-endotoxin genes to make them insect resistant.

The family of cry1 genes encode the Cry1 crystal proteins, which are primarily active against lepidopteran pests. The protoxin form of Cry1 delta-endotoxins comprises a C-terminal protoxin part, which is not toxic and is thought to be important for crystal formation (Arvidson et al., 1989). The amino-half of the protoxin comprises the active toxin segment of the Cry1 protein. Different domains have further been identified in the active toxin, which are implied in different aspects of the toxicity effect (Grochulski et al., 1995). However, these functions seem to be dependent on the delta endotoxin examined.

Significant effort has gone into modifying the cry1 genes to improve expression levels in plants while at least retaining their toxicity to the target insects. Modification of the cry1Ab and cry1Ac genes to remove putative plant polyadenylation signals and instability motifs (without altering the encoded amino acid sequences) resulted in increased resistance of the plants transformed with these sequences (van der Salm et al., 1994). Modifications of the cry1Ab gene have been described in U.S. Pat. No. 6,320,100, U.S. Pat. No. 6,180,774 and U.S. Pat. No. 6,114,608. U.S. Pat. No. 5,500,365 describes how modification in the 240 region of the coding region of a cry1Ab gene so as to remove putative plant signals is of significant importance to increase expression levels and thereby toxicity of the Cry toxin in plants.

The present invention relates to a novel modified Cry1Ab protein and DNA sequences encoding this protein, which can be used to engineer insect resistance in plants. More particularly, it was found that this modified sequence, despite having a native 240 region, ensures sufficiently high expression in plant cells to confer insect resistance to the plant or plant tissue in which it is expressed.

SUMMARY OF THE INVENTION

The present invention relates to a modified cry1Ab coding sequence, which encodes the modified Cry1Ab protein of SEQ ID NO: 1, which is an insecticidal protein. According to a particular embodiment of the invention, the DNA sequence encoding the modified Cry1Ab sequence corresponds to the sequence of SEQ ID NO: 2, or comprises the sequence of SEQ ID NO:2.

The invention further relates to chimeric genes comprising the modified cry1Ab DNA sequence of the present invention under the control of a plant-expressible promoter. According to a particular embodiment of the present invention the plant-expressible promoter is either a constitutive promoter, a tissue-specific promoter or a wound-inducible promoter or a promoter that ensures expression of the modified Cry1Ab protein at least in the cells or tissues of a plant which are susceptible to insect attack.

The invention further relates to recombinant vectors comprising the chimeric genes of the invention and to the production of transgenic plants using these recombinant vectors.

The invention further relates to plants and cells, seeds or tissues thereof, comprising in their genome a foreign DNA comprising the modified cry1Ab DNA sequence of the present invention under the control of a plant-expressible promoter.

The invention also relates to a method for engineering insect resistance in plants, by introducing, into the genome of the plant, a foreign DNA comprising the modified cry1Ab coding sequence of the present invention under the control of a plant-expressible promoter.

According to a particular embodiment of the present invention, the modified cry1Ab coding sequence is particularly suited for engineering insect resistance in agricultural crops such as corn and cotton. Most particularly, expression of the modified Cry1Ab protein confers resistance to lepidopteran pests of these plants. More particularly, these pests include, but are not limited to, major lepidopteran pests of corn, cotton and rice, such as *Ostrinia nubilalis* (European corn borer or ECB), *Sesamia nonagrioides* (Mediterranean Stalk borer), *Sesamia inferens* (Pink stemborer), *Helicoverpa zea* (corn earworm, cotton bollworm), *Helicoverpa armigera* (American bollworm), *Heliothis virescens* (Tobacco budworm), *Scirpophaga incertulas* (Yellow stemborer), and *Cnaphalocrocis medinalis* (Rice leaf folder).

DETAILED DESCRIPTION

The term "gene" as used herein refers to any DNA sequence comprising several operably linked DNA fragments such as a promoter region, a 5' untranslated region (the 5'UTR), a coding region, and an untranslated 3' region (3'UTR) comprising a polyadenylation site. A gene may include additional DNA fragments such as, for example, introns. While a promoter and a coding region are required in a gene used for plant transformation in the current invention, the 3' UTR comprising a polyadenylation site need not be present in the transferred gene itself, but can be recovered in the upstream plant DNA sequences after insertion of a gene not containing a 3' UTR comprising a polyadenylation site.

The term "chimeric" when referring to a gene or DNA sequence is used to refer to the fact that the gene or DNA sequence comprises at least two functionally relevant DNA fragments (such as promoter, 5'UTR, coding region, 3'UTR, intron) that are not naturally associated with each other and/or originate, for example, from different sources. "Foreign" referring to a gene or DNA sequence with respect to a plant species is used to indicate that the gene or DNA sequence is not naturally found in that plant, or is not naturally found in that genetic locus in that plant. The term "foreign DNA" will be used herein to refer to a DNA sequence as it has incorporated into the genome of a plant as a result of transformation.

A genome of a plant, plant tissue or plant cell, as used herein, refers to any genetic material in the plant, plant tissue or plant cell, and includes both the nuclear and the plastid and mitochondrial genome.

A "fragment" or "truncation" of a DNA molecule or protein sequence as used herein refers to a portion of the original DNA or protein sequence (i.e., nucleic acid or amino acid) referred to or a synthetic version thereof (such as a sequence which is adapted for optimal expression in plants), which can vary in length but which is sufficient to ensure the (encoded) protein is an insect toxin. A "variant" of a sequence is used herein to indicate a DNA molecule or protein of which the sequence (nucleic or amino acid) is essentially identical to the sequence to which the term refers.

Sequences which are "essentially identical" are similar to such a degree that when two sequences are aligned, the percent sequence identity, i.e. the number of positions with identical nucleotides or amino acids divided by the number of nucleotides or amino acids in the shorter of the sequences, is higher than 70%, higher than 85%, higher than 90%, higher than 95%, or is between 96% and 100%. The alignment of two nucleotide sequences is performed by the algorithm as described by Wilbur and Lipmann (1983) using a window size of 20 nucleotides, a word length of 4 nucleotides, and a gap penalty of 4.

A 'plant-expressible promoter' as used herein refers to a promoter that ensures expression of a coding sequence to which it is linked in a plant cell. Examples of such promoters are well known in the art. A plant-expressible promoter can be a constitutive promoter. Examples of promoters directing constitutive expression in plants are known in the art and include the 35S promoter from Cauliflower Mosaic virus, the nopaline synthase (NOS) promoter, the ubi promoter (Christensen et al. 1992), the promoter of the GOS2 gene from rice (de Pater et al., 1992). Alternatively, a plant-expressible promoter can be a tissue-specific promoter, i.e., a promoter directing a higher level of expression of a coding sequence (as can be measured by conventional RNA assays) in some tissues of the plant, e.g. in green tissues (such as the promoter of the PEP carboxylase) than in other tissues of the plant. Alternatively, a plant-expressible promoter can be a wound-inducible promoter. A 'wound-inducible' promoter or a promoter directing an expression pattern that is wound-inducible as used herein means that upon wounding of the plant, either mechanically or by insect feeding, expression of the coding sequence under control of the promoter is significantly increased. Examples of wound-inducible promoters include the proteinase inhibitor gene of potato and tomato (pin1 and pin2)(Johnson et al., 1989) and the promoter of the maize proteinase inhibitor (MPI) gene (Cordero et al. 1994).

The "TR2' promoter" as used herein relates to any promoter comprising the TR2' (or mannopine synthase, abbreviated as mas) functional part of the TR1'–TR2' dual promoter element from Agrobacterium (Velten et al. 1984; Langridge et al. 1989). Thus, the "TR2' promoter" can comprise the TR2' element either alone or in combination with all or part of the divergent TR1' element (Guevara-Garcia et al., 1998) or other (regulatory) elements. Such elements include, but are not limited to, enhancer regions, introns and the like, as long as the wound-induction characteristics in monocots, particularly corn, in accordance with the present invention are substantially retained. In one specific embodiment of this invention, transcription is directed from the TR2' promoter region (and the coding sequence is hence downstream of the TR2' promoter sequence), even if the TR1'–TR2' dual promoter (or any part thereof retaining the TR2' promoter element) is used.

'Insecticidal' is used herein to mean toxic to insects that are crop pests. More particularly, in the context of the present invention target insects are pests such as, but not limited to, major lepidopteran pests, such as *Ostrinia nubilalis* (European corn borer or ECB), *Sesamia nonagrioides* (Mediterranean Stalk borer), *Helicoverpa zea* (corn earworm, cotton bollworm), *Helicoverpa armigera* (American bollworm) and *Heliothis viriscens* (Tobacco budworm).

In one embodiment of the present invention, the DNA encoding an insecticidal crystal protein (ICP) is a modified cry1Ab DNA sequence encoding an ICP that is a modified Cry1Ab protein. The modified cry1Ab coding sequence may encode, for example, the modified Cry1Ab protein corresponding to the sequence of SEQ ID NO: 1. In an alternative embodiment of the invention the modified cry1Ab coding sequence corresponds to the sequence of SEQ ID NO: 2. The DNA sequence used for transformation of plants, particularly corn, cotton or rice, in accordance with the current invention, can also comprise other elements besides a coding region encoding the modified Cry1Ab protein of the invention. Such other elements may include a coding region encoding a transit peptide, a coding region encoding a selectable marker protein or a protein conferring resistance to a herbicide.

In one embodiment of the invention, the modified Cry1Ab protein is toxic to major lepidopteran pests of crops such as corn, cotton and rice. Plants according to the present invention, comprising a foreign DNA in their genome comprising a DNA encoding a modified Cry1Ab protein are protected against these pests, by expressing a controlling amount of this protein. The term "controlling" encompasses toxic (lethal) and combative (sublethal) amounts of Cry1Ab protein. At the same time, the plants according to the present invention are morphologically normal and may be cultivated in a usual manner for consumption and/or production of products. Furthermore, said plants substantially obviate the need for chemical or biological insecticides (to insects targeted by the modified Cry1Ab protein).

The expression level of an ICP in plant material can be determined in a number of ways described in the art. For example, expression can be measured by quantification of the mRNA encoding the insecticidal protein produced in the tissue using specific primers (such as described by Cornelissen & Vandewiele, 1989) or direct specific detection of the amount of insecticidal protein produced, e.g., by immunological detection methods. Alternatively, the expression level of a modified Cry1Ab protein according to the present invention may be represented as the percentage of soluble insecticidal protein as determined by immunospecific ELISA (for example, as described herein) related to the total amount of soluble protein (as determined, e.g., by Bradford analysis (Bradford, 1976)). An exemplary ELISA for use in measuring expression levels of ICP is a sandwich ELISA (Clark et al., 1986).

Different assays can be used to measure the insecticidal effect or efficacy of ICP expression in the plant. As noted above, the target insects of the ICP of the present invention are the major lepidopteran pests of agricultural crops such as corn, cotton and rice. Such target insects include, but are not limited to, the European Corn Borer (ECB) and *Sesamia nonagrioides* (SMG) in corn, the cotton bollworm (CBW) and tobacco budworm (TBW) in cotton, and the yellow stem borer, the pink stem borer and the rice leaf folder in rice. The toxicity of an ICP produced in a corn plant on ECB can be assayed in vitro by testing protein extracted from the plant in feeding bioassays with ECB larvae, or by scoring mortality of larvae distributed on leaf material of transformed plants in a petri dish (both assays as described by Jansens et al., 1997), or on plants isolated in individual cylinders. In the field first brood European corn borer (ECB1) infestation is evaluated based on leaf damage ratings (Guthrie, 1989) while evaluation of the total number of stalk tunnels per plant and stalk tunnel length are indicative of second brood (ECB2) stalk feeding damage.

Efficacy of the ICP produced in cotton plants transformed with a modified cry1Ab gene can also be measured using in vitro and/or in vivo assays. Toxicity of the transformed plant tissue to CBW larvae can be measured by feeding CBW larvae on squares, leaves or terminals and assaying weight of surviving larvae. In the field, plants are artificially infested with neonate CBW larvae and rating damage at regular intervals to leaves, terminals, squares, white bloom, and bolls (as described herein). It will be understood that similar assays can be developed for any target or non-target insect in order to determine efficacy of the ICP produced in the plant against such insect.

The plants of the present invention optionally also comprise in their genome a gene encoding herbicide resistance. The herbicide resistance gene may be the bar or the pat gene, which confers glufosinate tolerance to the plant, i.e. the plants are tolerant to the herbicide Liberty™. Tolerance to Liberty™. can be tested in different ways. For instance, tolerance can be tested by Liberty™ spray application. Spray treatments should be made between the plant stages V2 and V6 for best results (corn stages are as determined in 'How a Corn Plant Develops', Special Report No. 48, Iowa State University of Science and Technology, Cooperative Extension Service, Ames, Iowa, Reprinted June 1993). Tolerant plants are characterized by the fact that spraying of the plants with at least 200 grams active ingredient/hectare (g.a.i./ha), or 400 g.a.i./ha, and possibly up to 1600 g.a.i./ha (4×the normal field rate), does not kill the plants. A broadcast application should be applied at a rate of 28–34 oz Liberty™+3 lbs Ammonium sulfate per acre. It is best to apply at a volume of 20 gallons of water per acre using a flat fan type nozzle while being careful not to direct spray applications directly into the whorl of the plants to avoid surfactant burn on the leaves. The herbicide effect should appear within 48 hours and be clearly visible within 5–7 days.

Examples of other herbicide resistance genes are genes encoding resistance to phenmedipham (such as the pmph gene, U.S. Pat. No. 5,347,047; U.S. Pat. No. 5,543,306); genes encoding resistance to glyphosate (such as the EPSPS genes, U.S. Pat. No. 5,510,471); genes encoding bromoxynyl resistance (such as described in U.S. Pat. No. 4,810,648); genes encoding resistance to sulfonylurea (such as described in EPA 0 360 750); genes encoding resistance to the herbicide dalapon (such as described in WO 99/27116); genes encoding resistance to cyanamide (such as described in WO 98/48023 and WO 98/56238); and genes encoding resistance to glutamine synthetase inhibitors, such as PPT (such as described in EP-A-0 242 236, EP-A-0 242 246, EP-A-0 257 542).

Introduction of a foreign DNA into a plant cell can be obtained by conventional transformation methods described in the art. Such methods include, but are not limited to, Agrobacterium mediated transformation (U.S. Pat. No. 6,074,877, Hiei et al., 1997); microprojectile bombardment (as described, for example by Chen et al., 1994; Casas et al., 1995; Christou, 1997, Finer et al., 1999, Vasil et al. 1999); direct DNA uptake into protoplasts (as described, for example by De Block et al. 1989; Poulsen, 1996, Datta et al., 1999); electroporation (D'Halluin et al., 1992, U.S. Pat. No. 5,641,665; Bates, 1995); silicon whisker mediated DNA introduction (Dunwell, 1999); or other methods as generally reviewed by Potrykus (1990), Sawahel et al. (1995), Komari et al. (1998), Bogorad (2000) and Newell (2000).

The following non-limiting examples describe the development of a DNA sequence encoding a modified Cry1Ab protein, the construction of chimeric genes comprising this sequence for expression in plants, and insect resistant plants obtained therewith. Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY; in Volumes 1 and 2 of Ausubel et al. (1994) Current Protocols in Molecular Biology, Current Protocols, USA; and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences represented in the sequence listing:

SEQ ID NO: 1: Modified Cry1Ab protein
SEQ ID NO: 2: DNA sequence encoding a modified Cry1Ab protein

EXAMPLES

Development of a Modified Cry1Ab Gene

The modified Cry1Ab DNA sequence used herein encodes part of the Cry1Ab5 protein described by Hofte et al. (1986) corresponding to amino acid 1 to 616, which has an insertion of an alanine codon (GCT) 3' of the ATG start codon (AlaAsp2 . . . Asp616). The protein sequence of the modified Cry1Ab protein is provided in SEQ ID NO: 1. The sequence of the DNA encoding such a modified Cry1Ab protein is provided in SEQ ID NO: 2.

Cry1Ab Gene in Corn

Development of Cry1Ab Events in Corn

For Agrobacterium transformation of corn, constructs were developed wherein the cry1Ab coding sequence was placed under the control of different promoters: 35S promoter (Odell et al. 1985), the ubi promoter (Christensen et al. 1992), the promoter of the GOS2 gene from rice (de Pater et al., 1992) with the cab22 leader from Petunia (Harpster et al. 1988), the 5' leader sequence of the GOS2 gene from rice, containing the second exon, the first intron and the first exon of the GOS transcript (de Pater et al., 1992), or a TR2' promoter region (Velten et al. 1984); all constructs included the 35S-bar gene. Agrobacterium-mediated transformation was done by co-cultivation of type I callus derived from immature embryo's with strain C58C1 (pTiEHAE101) (pTTS35)(Agrobacterium C58C1RifR strain cured for pTiC58 harboring the non-oncogenic Ti plasmid pTiEHA101 (Hood et al., 1986) and the plasmids in the table below containing the genes of interest placed between the T-DNA borders).

le;2qProtoplast transformation was done by PEG mediated transfection of protoplasts prepared from suspension cultures derived from Pa91xH99xHE89 Z15 embryos. The DNA used for transfection was a purified fragment of the plasmids in the table below containing the genes of interest between T-DNA borders.

The expression of modified Cry1Ab protein in different tissues of early whorl plants transformed with the p35S-cry1Ab construct is provided in Table 1. Expression in the different progeny plants of one event obtained with p35S-cry1Ab event was found to be constitutive and above 0.5% on average.

TABLE 1

Expression of Cry1Ab in different tissues of the early whorl plant

| Event | Plant no | Leaf blade | Root |
|---|---|---|---|
| CP048-2602 | 0042 | 0.73 | 1.4 |
| (construct ptsvh0203) | 0032 | 1.12 | 3.18 |
|  | 0033 | 1.14 | 2.39 |
|  | 0034 | 1.12 | 2.65 |
|  | 0035 | 0.94 | 3.51 |
|  | 0039 | 0.88 | 2.48 |
|  | 0040 | 0.68 | 1.7 |
|  | 0036 | 0.27 | 0.81 |
|  | 0037 | 0.13 | 0.66 |
|  | 0038 | 0.15 | 1.15 |
|  | 0041 | 0.13 | 0.49 |
|  | 0043 | 0.08 | 0.78 |
|  | 0044 | 0.13 | 0.98 |
|  | 0045 | 0.08 | 0.55 |
|  | 0031 | 0.11 | 0.57 |
|  | Average (SD) | 0.51 (0.44) | 1.55 (1.03) |

|  | Construct description | Abbreviation |
|---|---|---|
| Agrobacterium transformation |  |  |
| PTSVH0203 | P35S2-GE1-modcry1Ab-3'ocs<>p35S3-bar-3'nos | p35S-cry1Ab |
| PTSVH0207 | Pubi1-ubi leader with intron-modcry1Ab-3'ocs<>p35S3-bar-3'nos | pUbi-cry1Ab |
| PTSVH0208 | Pgos2-cab22 leader-modcry1Ab-3'ocs<>p35S3-bar-3'nos | pGos-cab-cry1Ab |
| PTSVH0209 | Pgos2-gos leader with intron-modcry1Ab-3'ocs<>p35S3-bar-3'nos | pGos-gos-cry1Ab |
| PTSVH0212 | 3'nos-bar-p35S3><Tr2-modcry1Ab-3'ocs | pTR2-cry1Ab |
| Protoplast transformation |  |  |
| PSVH0211 | Pubi1-ubi leader with intron-cry1Ab53-3'ocs<>p35S3-bar-3'nos | pUbi-cry1Ab |
| PSVH0213 | Pgos2-gos leader with intron-modcry1Ab-3'ocs<>p35S3-bar-3'nos | pGos-gos-cry1Ab |

Regenerated plantlets were selected based on Liberty tolerance and/or measurement of PAT protein levels by ELISA (Clark et al, 1986).

Evaluation of Events

General Characterization

The Agrobacterium transformants were checked for presence of vector sequence at the left border of the T-DNA. Southern blot analyses were performed with leaf material of the primary transformants (T0).

Expression of Modified Cry1Ab Protein

The events were analyzed in the greenhouse for Cry1Ab expression by detecting soluble modified Cry1Ab protein levels in different tissues by a Cry1Ab sandwich ELISA with a polycondensated IgG fraction of a polyclonal rabbit antiserum against Cry1Ab as first antibody and a monoclonal antibody against Cry1Ab as second antibody.

The expression levels of Cry1Ab protein in different tissues in early V, R1 and R4-5 stage leaves, R4-5 stage kernels and in pollen for plants transformed with the p35S-cry1Ab, pGos-cab-cry1Ab and pTR2-cry1Ab constructs are provided in Table 2. Results are presented as averages of leaf and kernel samples taken from five plants and as averages of pollen samples taken from three plants (standard deviation in brackets). ICP expression for the one p35S-cry1Ab plant is above 0.1% total soluble protein. The pGos-cab-cry1Ab plants showed around 0.01–0.06% Cry1Ab expression in leaves. The events obtained with the pGos-gos-cry1Ab constructs showed high expression (0.2–0.6% protein) in leaf tissue. Basal expression of protein in leaves of plants transformed with the modified cry1Ab DNA sequence under control of the wound-inducible TR2' promoter (pTR2'-cry1Ab) was low to undetectable.

TABLE 2

Expression of Cry1Ab protein in different tissues of plants transformed with the Cry1Ab gene Cry1Ab in % soluble protein/total protein

| Event | Construct | 5 plants early V/leaf | 5 plants R1/leaf | 3 plants pollen | 5 plants R4–5/leaf | 5 plants R4–5/kernel |
|---|---|---|---|---|---|---|
| CE048-2602 | p35S-cry1Ab | 0.186 (0.066) | 0.54 (0.38) | 0 | 0.41 (0.17) | 0.048 (0.039) |
| CE104-0202 | pGos-cab-cry1Ab | 0.014 (0.0055) | | | 0.036 (0.015) | |
| CE1014-0402 | pGos-cab-cry1Ab | 0.032 (0.016) | | | 0.041 (0.011) | |
| CE122-0806 | pGos-cab-cry1Ab | 0.024 (0.015) | 0.10 (0.013) | 0 | 0.058 (0.036) | 0 (0) |
| CE2162-0402 | pGos-gos-cry1Ab | 1.27 (0.82) | | | | |
| CE2168-0202 | pGos-gos-cry1Ab | 0.467 (0.23) | | | | |
| CE2168-1218 | pGos-gos-cry1Ab | 0.26 (0.026) | | | | |
| CE21612-1402 | pGos-gos-cry1Ab | 0.158 (0.067) | 0.256 (0.106) | 0 | 0.153 (0.023) | 0.017 (0.006) |
| CE21614-0604 | pGos-gos-cry1Ab | 0.682 (0.50) | | | | |
| CE21614-0816 | pGos-gos-cry1Ab | 0.327 (0.27) | 0.925 (0.198), 1 plant 0.06 | 0.036 (0.0115) | 0.44 (0.078) | 0.0417 (0.021) |
| CP21614-1606 | pGos-gos-cry1Ab | 0.38 (0.153) | | | | |
| WI600-0218 | pTR2-cry1Ab | 0 | 0 | 0 | 0 | 0.002 |
| WI600-0802 | pTR2-cry1Ab | 0 | 0 | 0 | 0.0048 (0.0016) | 0.01 |

In a greenhouse study, expression of modified Cry1Ab protein was determined in leaf samples of plants in V3 stage, and, where available, leaf and pollen of plants in R1 stage, and leaf, stalk and pollen of plants at harvest, for events obtained with the different constructs. Again, the plants with the pGos-gos-cry1Ab constructs showed high Cry1Ab expression in leaves (>0.2% total soluble protein) (irrespective of transformation method used). For these plants, high expression levels were also found in the stalk (0.8% total soluble protein or more on average). Events obtained from transformation with the pTR2'-cry1Ab constructs showed low (0.02% total soluble protein or less on average) or undetectable expression of Cry1Ab protein in all tissues tested.

Inducible Cry1Ab Expression

For the events obtained with the pTR2'-cry1Ab construct, studies were performed in the greenhouse to determine the expression of the Cry1Ab protein upon mechanical damage. Leaf samples were taken before wounding, and 18 h after mechanical damage and Cry1Ab protein levels were measured by ELISA (Table 3). Damaged leaf parts were excised and incubated for 18 hours in a petri dish on filter paper moistened with Murashige and Skoog (MS) medium (Plant Molecular Biology Labfax (1993) by R. D. D. Croy, jointly published by BIOS Scientific Publications Ltd (UK) and Blackwell Scientific Publications, UK) at room temperature and then Cry1Ab protein level was measured using a sandwich ELISA assay. Unwounded control leaf parts (of similar size as the wounded leaf parts) were excised from the plants and were immediately put on dry ice for protein analysis.

TABLE 3

Expression of insecticidal protein in different plant parts before and after mechanical wounding Cry1Ab in % soluble protein/total protein

| Event (construct) | | V4 stage | | Flowering | | | | | Harvest | | |
|---|---|---|---|---|---|---|---|---|---|---|---|
| | | Leaf | | Leaf | | Root | | | | | |
| | | Leaf | induced | Leaf | induced | root | induced | Pollen | Leaf | Stalk | Kernel |
| WI600-0218 | Mean | 0.000 | 0.020 | 0.000 | 0.020 | 0.023 | 0.036 | 0.000 | 0.000 | 0.000 | 0.000 |
| (pTR2'-Cry1Ab) | st.dev. | 0.000 | 0.008 | 0.000 | 0.007 | 0.008 | 0.011 | 0.000 | 0.000 | 0.000 | 0.000 |
| WI606-0406 | Mean | 0.005 | 0.046 | 0.000 | 0.007 | 0.012 | 0.008 | 0.000 | \ | 0.002 | 0.002 |
| (pTR2'-Cry1Ab) | st.dev. | 0.007 | 0.005 | 0.000 | 0.006 | 0.009 | 0.009 | 0.000 | | 0.004 | |
| WI604-1602 | Mean | 0.002 | 0.104 | 0.001 | 0.020 | 0.020 | 0.024 | 0.000 | 0.004 | 0.004 | 0.001 |
| (pTR2'-Cry1Ab) | st.dev. | 0.003 | 0.012 | 0.000 | 0.009 | 0.008 | 0.008 | 0.000 | 0.002 | 0.003 | 0.000 |
| WI606-0802 | Mean | 0.003 | 0.064 | 0.001 | 0.010 | 0.027 | 0.037 | 0.000 | 0.002 | 0.004 | 0.003 |
| (pTR2'-Cry1Ab) | st.dev. | | 0.004 | 0.000 | 0.009 | 0.012 | 0.020 | 0.000 | 0.001 | 0.003 | 0.001 |
| WI606-1206 | Mean | 0.001 | 0.081 | 0.000 | 0.022 | 0.032 | 0.024 | 0.000 | 0.004 | 0.002 | 0.001 |
| (pTR2'-Cry1Ab) | st.dev. | | 0.016 | 0.000 | 0.010 | 0.005 | 0.011 | 0.000 | 0.003 | 0.001 | 0.001 |
| CE048-2402 | Mean | 0.83 | 0.614 | 0.280 | 0.397 | 0.196 | 0.253 | 0.000 | 0.376 | 1.120 | 0.047 |
| (p35S-Cry1Ab) | st.dev. | 0.108 | 0.111 | 0.027 | | 0.133 | 0.083 | 0.000 | 0.098 | 0.175 | 0.014 |
| CE048-2602 | Mean | 0.636 | 0.527 | 0.007 | 0.006 | 0.087 | 0.045 | 0.000 | 0.106 | 0.040 | 0.015 |
| (p35S-Cry1Ab) | st.dev. | 0.16 | 0.046 | 0.002 | 0.002 | 0.044 | 0.007 | 0.000 | 0.011 | 0.013 | 0.004 |
| Control 1 | Mean | 0.000 | 0.000 | 0 | 0 | 0 | 0 | 0 | 0 | 0.001 | 0 |
| (untransformed) | st.dev. | 0.000 | 0.000 | 0 | 0 | 0 | 0 | 0 | 0 | 0.002 | 0 |
| Control 2 | Mean | 0.000 | 0.000 | 0 | 0 | 0 | 0 | 0 | 0 | 0 | 0 |
| (untransformed) | st.dev. | 0.000 | 0.000 | 0 | 0 | 0 | 0 | 0 | 0 | 0 | 0 |
| CE0104-0202 | Mean | 0.022 | 0.023 | 0.008 | 0.017 | 0.023 | 0.016 | 0.0001 | \ | \ | \ |

TABLE 3-continued

Expression of insecticidal protein in different plant parts before and after mechanical wounding

| | | Cry1Ab in % soluble protein/total protein | | | | | | | | | |
|---|---|---|---|---|---|---|---|---|---|---|---|
| | | V4 stage | | Flowering | | | | | Harvest | | |
| Event | | Leaf | | Leaf | | Root | | | | | |
| (construct) | | Leaf | induced | Leaf | induced | root | induced | Pollen | Leaf | Stalk | Kernel |
| (pGos/cab-Cry1Ab) | st.dev. | 0.009 | 0.005 | 0.005 | 0.004 | 0.012 | 0.005 | 0.000 | | | |
| CE1014-0402 (pGos/cab-Cry1Ab) | Mean | 0.025 0.005 | 0.017 0.003 | 0.007 0.001 | 0.010 0.003 | 0.028 0.017 | 0.034 0.013 | 0.000 0.000 | 0.010 0.003 | 0.040 0.020 | 0.002 0.001 |

Expression of the Cry1Ab protein was either absent or around the detection limit in leaves, stalk and kernels of the different pTR2' events tested. No expression above background levels (as found in untransformed control plants) was found in leaves and pollen in whorl and pollen shedding plant stage. Constitutive expression was seen in the roots. When leaves are mechanically damaged, expression of the modified Cry1Ab protein is induced and goes up to 0.02–0.1% in V4 stage leaves.

ECB Efficacy

ECB efficacy trials were performed in the greenhouse and at two different locations in the field. At the same time, plants were evaluated for phytotoxicity effects of the constructs introduced. Table 4 shows the results of efficacy tested for ECB. In the greenhouse, ECB efficacy is determined by measuring the length of tunnels in cm per stalk for 10 plants and is expressed as the average length (sd in brackets) of tunnels per maximum number of tunnels per plant. In the field, ECB efficacy is expressed as the average of 3 values obtained for different groups of 10 plants.

TABLE 4

ECB efficacy trials in the greenhouse and in different locations in the field

| | Greenhouse ECB efficacy | Field 1 ECB efficacy | Field 2 ECB Efficacy |
|---|---|---|---|
| p35S-cry1Ab | | | |
| CE024-1301 PGos-cab-cry1Ab | 1.2 (1.47)/2 | 0.4 (0.53)/4 | 0.05 (0.07)/1 |
| CE050-0802 | 0 (0)/0 | 0 (0)/0 | 0 (0)/14 |
| CE052-0101 | 0.6 (0.84)/2 | 0.37 (0.43)/3 | 0.17 (0.23)/2 |
| CE052-0205 | 1.6 (2.4)/6 | 0.08 (0.072)/1 | 0.05 (0.07)/2 |
| CE053-0605 | 0.4 (0.69)/2 | 0.113 (0.1)/1 0.09 (0.085)/1 | 0.047 (0.08)/1 0 (0)/0 |
| CE053-0702 | 0.6 (0.96)/2 | 0.4 (0.53)/5 | 0.055 (0.097)/1 |
| CE057-0201 | | 0.21 (0.26)/1 | 0.2 (0.35)/6 |
| CE060-0402 | 0.7 (1.64)/5 | 0.91 (0.44)/4 | 0.4 (0.692)/3 |
| CE061-0301 | 0.7 (1.16)/3 | 0.22 (0.39)/4 | 0.0625 (0.088)/1 |
| CE061-1102 | 2.7 (1.76)/5 | 1 | |
| CE061-1402 | 2.8 (4.52)/8 | | 0.22 (0.47)/2 |
| CE061-1502 | 1.7 (0.97)/(3) | 0.08 (0.14)/1 | 0 (0)/0 |
| CE062-0201 | 0 (0)/0 | 0 (0)/0 | 0 (0)/0 |
| CE067-0401 | | 0 (0)/0 | 0.205 (0.113)1 |
| CE068-0903 pGos-gos-Cry1Ab | | 0.07 (0.11)/2 | 0.04 (0.0072)/1 |
| CE180-0303 | 0 (0)/0 | 0 (0)/0 | 0 (0)/0 |
| CE181-0201 | 0.1 (0.32)/1 | 0.36 (0.34)/2 | 0 (0)/0 |

TABLE 4-continued

ECB efficacy trials in the greenhouse and in different locations in the field

| | Greenhouse ECB efficacy | Field 1 ECB efficacy | Field 2 ECB Efficacy |
|---|---|---|---|
| CE182-0101 | | 0 (0)/0 | 0.07 (0.1)/0 |
| CE183-0501 | | 0 (0)/0 | 00.056 (0.08)/1 |
| CE183-0601 | | 1 | 0 (0)/0 |
| CE184-0101 | 0.7 (1.06)/3 | 0.51 (0.35)/2 | 0 (0)/0 |
| CE184-0609 | | 0 (0)/0 | 0 (0)/0 |
| CE184-0801 | 0.11 (0.33)/1 | 0 (0)/0 | 0 (0)/0 |
| CE186-0203 | | 0 (0)/0 | 0.037 (0.064)/1 |
| CE187-0302 | | 0.08 (0.14)/2 | 0 (0)/0 |
| CE187-0408 | 0.1 (0.32)/1 | 0 (0)/0 | 0.11 (0.19)1 |
| CE187-0803 | | 0.096 (0.17)/1 | 0.097 (0.16)1 |
| CE193-1002 | | 0.15 (0.17)/1 | 0.33 (0.58)/4 |
| CE196-0201 | 0.4 (1.26)/0 | 0 (0)/0 | 0.144 (0.14)1 |
| CE197-0102 | | 0 (0)/0 | |
| CE198-0401 | 0.9 (1.28)/3 | 0.09 (0.08)/1 | 0 (0)/0 |
| CE198-0802 | 0 (0)/0 | 0.17 (0.21)/3 | 0.03 (0.057)/1 |
| CE198-1401 | 0 (0)/0 | 0.047 (0.0082)/1 | 0 (0)/0 |
| CE198-1702 | 0.1 (0.32)/1 | 0.55 (0.74)/4 | 0 (0)/0 |
| CE198-2101 | 0.1 (0.32)/1 | 0 (0)/0 | 0.085 (0.12)1 |
| CE198-2501 PUbi-cry1Ab | 0 (0)/0 | 0 (0)/0 | 0 (0)/0 |
| ACE054-00103 | 158.8 (32.3)/200 | 19.0 (1.4)30 | |
| ACE054-01502 | 166.2 (31.2)/235 | 20.7 (0.98)/27 | |
| ACE054-02803 | 114.5 (92.1)/270 | 22.4 (2.9)/42 | |
| B73 control | 150.6 (40.3)/211 | 25.7 (4.8)/39 | 27.6 (7.4)/62 |

The p35S-cry1Ab event gave absolute ECB control, both in the greenhouse as in field-trials at different locations which correlated with the high-dose expression (as described above). Similarly, the pGos-gos-cry1Ab and PGos-cab-cry1Ab events displayed good ECB control at all locations tested. The pUbi-cry1Ab event did not show good ECB control.

No phytotoxicity was observed for any of the p35S-cry1Ab or pGos-cab-cry1Ab events. Selfed seed of pGos-gos-cry1Ab events showed segregation in the field of normal green plants and stunted, yellowish plants, from which the lower leaves are dying, suggestive of some impact on agronomic performance.

Fourteen events obtained with the pTR2'-cry1Ab construct were evaluated for ECB efficacy in the greenhouse and in field trials (Table 5). Four of the five single-copy events (indicated with an asterisk) gave total ECB2 control.

TABLE 5

ECB Efficacy in the Greenhouse and in the Field for pTR2'-cry1Ab events

| Event | ECB efficacy Greenhouse Average (sd)/max tunnels/pl | ECB efficacy Field average (sd)/max tunnels/pl | ECB efficacy Field Average (sd)/max tunnels/pl |
|---|---|---|---|
| WI602-0402 | 0.1 (0.31)/1 | 0.24 (0.41)/2 | 0.21 (0.01)/2 |
| WI604-1602 | 0.2 (0.42)/1 | 0.05 (0.071)/1 | |
| WI606-0406* | 51.3 (73.5)/195 | 8.41 (1.8)/32 | 7.45 (0.07)/30 |
| WI606-0802 | 3.3 (2.6)/8 | 0 (0)/0 | 0.05 (0.07)/1 |
| WI606-1206 | 0.38 (0.74)/2 | 0.17 (0.29)/3 | 0.1 (0.14)/1 |
| WI600-0218 | 2.0 (1.87)/6 | | |
| WI600-1402* | 29.4 (45.8)/142 | 6.55 (2.47)/28 | |
| WI602-0202* | 168.5 (26.9)/200 | 12.6 (3.8)/31 | |
| WI604-0604* | 102.5 (83)/251 | 3.7 (2.0)/25 | |
| WI602-0802 | 0 (0)/0 | 0.33 (0.15)/3 | |
| WI602-0204 | 66 (68.2)/160 | | |
| WI602-1002 | 102.4 (63.4)/215 | | |
| WI606-0602 | 45.5 (52.8)/160 | | |
| WI600-0802 | 0.9 (1.44)/4 | 0.06 (0.11)/2 | 0 (0)/0 |
| B73 control | 150.6 (40.3)/211 | 25.7 (4.8)/39 | 27.6 (7.4)/62 |

No penalty on agronomic performance was observed for the plants after second selfing (ear to row) of the different TR2' events in any of the locations tested.

Efficacy Against *Sesamia nonagrioides*

Five mid whorl corn plants obtained with the pTR2'-cryl Ab construct were each infested with 2 egg masses. Damage was scored after 14 days and the number of larvae were counted. Damage ratings were averaged over the five plants. Non-transformed B73 plants were similarly infested as controls. Results are shown in Table 6.

TABLE 6

| Event | Number of larvae per plant | Plant height in cm | Cm tunnels per plant |
|---|---|---|---|
| WI600-0802 | 0.6 (1.3) | 198 (8.4) | 0 |
| B73 Control | 197.2 (14.0) | 84 (5.5) | 70 (9.4) |

Example 3

Cry1Ab Gene in Cotton

I. Development of Cry1Ab Events in Cotton

A construct was made for the expression of the modified cry1Ab gene in cotton. The pTSVH0203 construct contains the modified cry1Ab coding sequence (encoding part of the Cry1Ab5 protein described by Höfte et al. 1986 having an insertion of an alanine codon (GCT) 3' of the ATG start codon). The cry1Ab coding sequence is under control of the constitutive promoter 35S (Odell et al. 1985), linked to the leader sequence of the tapetum E1 gene from *Oryza sativa* (WO92/13956) with the 3' ocs terminator (fragment containing polyadenylation signals from the 3'untranslated region of the octopine synthase gene from the TL-DNA of pTiAch5, De Greve et al., 1983). The construct additionally comprises the bar coding sequence (the coding sequence of phosphinothricin acetyl transferase of *Streptomyces hygroscopicus*; Thompson et al., 1987) under control of the 35S promoter.

| PTSVH0203 | P35S2-GE1-cry1Ab53-3'ocs<>p35S3-bar-3'nos | p35S-cry1Ab-ocs |
|---|---|---|

This construct was used for transformation of cotton. The obtained events were subjected to molecular analysis to confirm presence of the transgene.

Analysis of Events

1. Expression of Modified Cry1Ab Protein

Expression of modified Cry1Ab protein was determined in leaf, terminal, square, flower and boll samples using ELISA (Table 7). Results represent percentage of Cry1Ab protein of total protein content as an average of samples taken from 9 plants. The time point at which samples were taken is represented as days after planting (in brackets).

TABLE 7

Cry1Ab expression as measured by ELISA in different tissues

ELISA, Cry1Ab expression in %, 9 plants

| Events | Leaf (60) | Leaf (65–80) | Leaf (115–120) | Terminal leaf (60) | Terminal leaf (65–80) | Terminal leaf (115–120) | Squares (60) | Flower (65–80) | Bolls (115–120) |
|---|---|---|---|---|---|---|---|---|---|
| COCE040-04702A | 0.024 | 0.008 | 0.005 | 0.005 | 0.012 | 0.006 | 0.002 | 0.003 | 0 |
| COCE040-04702B | | 0.011 | | | | | | | |
| COCE040-3106-1143 | 0.017 | 0.022 | 0.012 | 0.015 | 0.011 | 0.007 | | 0.003 | |
| COCE040-3106-1144 | | 0.018 | | | | | | | |

2. Laboratory Toxicity Assay

CBW larvae were fed on squares, leaf and terminals obtained from leaves in the field. Weight of surviving larvae was measured for the different events (Table 8). Samples from two non-transgenic plants and from one plant comprising a herbicide resistance gene (LL25 event) were used as control

TABLE 8

Toxicity of modified Cry1Ab expressed in cotton to CBW larvae

| | Weight in mg of surviving larvae | | |
|---|---|---|---|
| Event | Squares | Terminals | Leaf |
| 5 | 2.8 | 0 | 8.7 |
| 8 (- control LL25) | 22.3 | 1.7 | 15.5 |
| 11 | 0 | 0 | 18 |
| 13 | 4.3 | 1 | 20.6 |
| 16 | 6 | 0.3 | 23 |
| 21 (- control non-transgenic) | 16.5 | 8.7 | 26.3 |
| 23 (- control non-transgenic) | 8.2 | 38.5 | 29 |

3. Efficacy of Insect Control in the Field

In the field, plants were artificially infested with neonate CBW larvae. Damage to leaves, terminals, squares, white bloom and bolls was rated and counts were made each 8 days in August and September. A mean was made over the five observations dates. Statistical analysis indicated that significant differences were found in the mean damage severity of terminals, white blooms and bolls. In addition, the mean number of damaged squares and damaged bolls was higher for the controls than for the Cry1Ab events; The mean number of larvae in squares was also significantly reduced compared to controls.

Example 4

Cry1Ab Gene in Rice

A construct was made for the expression of the modified cry1Ab gene in rice. The construct contains the modified cry1Ab coding sequence (encoding part of the Cry1Ab5 protein described by Höfte et al. 1986 having an insertion of an alanine codon (GCT) 3' of the ATG start codon). In this construct, the cry1Ab coding sequence is under control of the promoter with the 5' leader sequence of the GOS2 gene from rice, containing the second exon, the first intron and the first exon of the GOS transcript (de Pater et al., 1992). This construct was used for transformation of rice. The obtained events were subjected to molecular analysis to confirm presence of the transgene.

Plants of 25 different events were tested for control of rice leaf folder, yellow stem borer, and pink stem borer by counting the number of surviving larvae. Damage to the plants was assessed as damage to the leaves (for leaf folder) or the number of deadhearts per number of tillers at the preflowering stage (yellow stem borer and pink stem borer) or the number of whiteheads per number of tillers at the flowering stage (yellow stem borer). For only 2 events plants were found on which some (5–7 out of 25) of the larvae survived. All plants of all other events showed 90–100% dead larvae. While the control plants were either completely dried up or showed many folded leaves when infested with rice leaf folder, none of the plants of the cry1Ab events showed any significant damage. Similarly, no deadhearts or whiteheads were detected for the plants of the cry1Ab events, infested with yellow stem borer or pink stem borer.

REFERENCES

Arvidson et al., 1989, Mol Microbiol 3:1533
Barton et al. 1987, Plant Physiol 85:1103–1109
Bates, 1995, Methods Cell Biol. 1995;50:363–73
Bogorad 2000, Trends Biotechn 18(6):257–263
Bradford, 1976, Anal. Biochem. 72: 248–254
Breitler et al. 2001, Mol Breeding 7: 259–274
Casas et al., 1995, Plant Breed Rev 13:235–264
Chen et al., 1994, Theor Appl Genet 88:187–192
Christensen et al. 1992, Plant Mol Biol 18(4):675–89
Christou, 1997, Plant Mol Biol 35(1–2):197–203
Clark et al., 1986, Methods Enzymol. 118:742–766.
Cordero et al. 1994, Plant J 6(2):141–50.
Cornelissen & Vandewiele, 1989, Nucleic Acids Research 17:19–23
Crickmore et al. 1995, 28$^{th}$ Annual Meeting of the Society for Invertebrate Pathology, Society for Invertebrate Pathology, Bethesda, Md, p 14
D'Halluin et al., 1992, Plant Cell 4: 1495–1505
Datta et al., 1999, Methods Mol Biol 111:335–347
De Block et al. 1989, Plant Physiol 914:694–701
De Greve et al., 1983, J Mol Applied Gen: 499–511
De maagd et al. 1999, Trends Plant Sci 4:9–13
de Pater et al., 1992, Plant J 2:837–844
Depicker et al., 1982, J Mol Appl Gen 1: 561–573
Duan et al., 1996, Nature Biotech 14:494–498
Dunwell, 1999, Methods Mol Biol 111: 375–82
Finer et al., 1999, Cur Top Micriobiol Immunol 240:59–80
Franck et al. 1980, Cell 21: 285–294
Grochulski et al., 1995, J Mol Biol 254:447
Guevara-Garcia et al., 1998, Plant J 4(3):495–505
Guthrie, 1989, Plant Breed Rev 6:209–243
Harpster et al. 1988, Mol Gen Genetics 212:182
Hiei et al., 1997, Plant Mol Biol 35:201–218
Hofte and Whiteley, 1989, Microbiol Rev 53(2):242–55
Höfte et al., 1986, EurJ Biochem 161:273–280
Hood et al., 1986. J. Bacterial. 168: 1291
Jansens et al., 1997, Crop Science 37(5):1616–1624
Johnson et al., 1989, PNAS 86:9871
Komari et al. 1998, Curr Opin Plant Biol 1(2):161–165
Langridge et al. 1989, Proc Natl Acad Sci USA 86:3219–3223
Newell, 2000, Mol Biotechnol 16(1):53–65
Odell et al., 1985, Nature 313: 810–812
Potrykus 1990, Cyba Found Symp 154:198–208
Poulsen, 1996, Plant Breeding 115:209–225
Sawahel et al. 1995, Biotechniques 19(1):106–110
Schnepf et al., 1998, Microbiol Mol Biol Rev 62:775–806
Thompson et al., 1987, EMBO J 6: 2519–2523
van der Salm et al., 1994, Plant Mol Biol 26:51
Vasil et al. 1999, Methods Mol Biol 111:349–358
Velten et al. 1984, EMBO J. 12:2733–2730
Wilbur and Lipmann, 1983, Proc Natl Acad Sci U.S.A. 80:726
Witowsky & Siegfried, 1997, PBI Bulletin 14–15

The invention claimed is:

1. A DNA sequence comprising a coding region encoding a modified Cry1Ab protein, wherein the DNA sequence comprises the nucleotide sequence of SEQ ID NO: 2.

2. An isolated chimeric gene comprising the DNA sequence of claim 1 under control of a plant-expressible promoter.

3. A recombinant vector comprising the chimeric gene of claim 2.

4. A transgenic plant cell comprising the chimeric gene of claim 2.

5. A transgenic plant comprising the plant cell of claim 4.

6. The transgenic plant of claim 5, which is corn, cotton, or rice.

7. A seed of the plant of claim 6, wherein the seed comprises the DNA sequence of SEQ ID NO: 2.

8. A method for protecting a plant from lepidopteran insects pests, wherein the method comprises introducing into the plant the chimeric gene of claim 2 in a manner such that the plant produces an insect-controlling amount of the modified Cry1Ab protein.

9. A method for protecting a plant from Lepidopteran insects, comprising growing a plant in a field, wherein said plant produces an insect-controlling amount of a modified insecticidal crystal protein comprising the amino acid sequence of SEQ ID NO: 1 in cells of said plant, wherein the cells comprise a chimeric gene comprising the DNA sequence of SEQ ID NO: 2 under control of a plant-expressible promoter.

10. The method of claim 9, wherein the cells comprise a chimeric gene comprising the DNA sequence of SEQ ID NO:2 under control of a plant-expressible promoter.

* * * * *